(12) United States Patent
Hickenbotham

(10) Patent No.: US 9,345,549 B2
(45) Date of Patent: May 24, 2016

(54) DEVICES AND METHODS FOR IMPROVING VISION USING LASER PHOTOMIOSIS

(71) Applicant: ThruFocus Optics, Inc., Richmond, CA (US)

(72) Inventor: Adam L. Hickenbotham, Richmond, CA (US)

(73) Assignee: THRUFOCUS OPTICS, INC., Richmond, CA (US)

( * ) Notice: Subject to any disclaimer, the term of this patent is extended or adjusted under 35 U.S.C. 154(b) by 97 days.

(21) Appl. No.: 13/775,071

(22) Filed: Feb. 22, 2013

(65) Prior Publication Data

US 2013/0226161 A1  Aug. 29, 2013

Related U.S. Application Data

(60) Provisional application No. 61/603,281, filed on Feb. 25, 2012.

(51) Int. Cl.
```
A61F 9/007    (2006.01)
A61F 9/008    (2006.01)
A61B 19/00    (2006.01)
```
(52) U.S. Cl.
CPC .......... *A61B 19/50* (2013.01); *A61F 9/008* (2013.01); *A61F 9/00745* (2013.01); *A61F 9/00829* (2013.01); *A61F 9/00838* (2013.01); *A61F 2009/00876* (2013.01); *A61F 2009/00897* (2013.01)

(58) Field of Classification Search
CPC ..... A61F 9/008; A61F 9/013; A61F 9/00745; A61F 9/0082; A61F 9/00838; A61F 2009/00895; A61F 2009/00897; A61F 2009/00876; A61F 2009/00887; A61F 2009/00891; A61B 18/14; A61B 19/50
USPC ........................................................ 606/4–6
See application file for complete search history.

(56) References Cited

U.S. PATENT DOCUMENTS

| | | | |
|---|---|---|---|
| 3,930,504 A | | 1/1976 | De Laforcade |
| 5,549,596 A | * | 8/1996 | Latina .............................. 606/4 |
| 6,258,082 B1 | * | 7/2001 | Lin .................................. 606/5 |

(Continued)

OTHER PUBLICATIONS

Bhattacharyya et al., Step by Step, Laser in Opthamology, 2009, Jaypee Brothers Medical Publishers (P) Ltd, First Edition, pp. 143-147.*

(Continued)

*Primary Examiner* — Gary Jackson
*Assistant Examiner* — Boniface N Nganga
(74) *Attorney, Agent, or Firm* — Morgan, Lewis & Bockius LLP

(57) ABSTRACT

Systems and methods of improving vision using an ophthalmological laser system are provided. A predetermined pattern characterized by a plurality of positions along a plurality of spatially distributed iris tissues of an eye of a patient is obtained. A laser illumination light beam is aligned in accordance with one or more of the plurality of positions along the plurality of spatially distributed iris tissues. The laser illumination light beam is delivered in the predetermined pattern to the plurality of spatially distributed iris tissues of the patient. At least a subset of the spatially distributed iris tissues is cauterized by the delivery of the laser illumination light beam in the predetermined pattern, thereby resulting in a permanent decrease in diameter of the pupil of the eye.

24 Claims, 10 Drawing Sheets

(56) References Cited

U.S. PATENT DOCUMENTS

| | | | |
|---|---|---|---|
| 6,263,879 B1* | 7/2001 | Lin | 128/898 |
| 6,325,792 B1* | 12/2001 | Swinger et al. | 606/4 |
| 6,357,875 B1 | 3/2002 | Herrick | |
| 2002/0101564 A1 | 8/2002 | Herrick | |
| 2002/0161365 A1 | 10/2002 | Martins | |
| 2002/0167644 A1* | 11/2002 | Pollack et al. | 351/219 |
| 2004/0030269 A1* | 2/2004 | Horn et al. | 601/2 |
| 2005/0049584 A1 | 3/2005 | Homer | |
| 2005/0165385 A1* | 7/2005 | Simon | 606/4 |
| 2005/0205101 A1* | 9/2005 | Lin | 128/898 |
| 2008/0015553 A1 | 1/2008 | Zacharias | |
| 2008/0243108 A1* | 10/2008 | Murakami et al. | 606/4 |
| 2009/0051872 A1* | 2/2009 | Volk | 351/219 |
| 2010/0016395 A1* | 1/2010 | Benozzi | 514/397 |
| 2011/0160622 A1 | 6/2011 | McArdle | |
| 2012/0265180 A1* | 10/2012 | Homer | 606/4 |
| 2013/0289450 A1* | 10/2013 | Homer | 601/2 |
| 2014/0128854 A1* | 5/2014 | McArdle et al. | 606/4 |
| 2014/0148737 A1 | 5/2014 | Homer | |
| 2014/0228825 A1* | 8/2014 | Gorschboth et al. | 606/5 |

OTHER PUBLICATIONS

S. S Mohammad, "Lasers Uses in Opthamology", 1997, Journal of Postgraduate Medical Institute (JPMI) vol. 11 No. 2 pp. 111-123.*

Hill, R.A. et al., "Ab-Interno Erbium (Er): YAG Laser Sclerostomy with Iridotomy in Dutch Cross Rabbits", Lasers in Surgery and Medicine, vol. 13, No. 5, pp. 559-564, Jan. 1, 1993.

Supplementary European Search Report, EP Application No. 13751556, for Thrufocus Optics, Inc., dated Jan. 11, 2016.

* cited by examiner

US 9,345,549 B2

DEVICES AND METHODS FOR IMPROVING VISION USING LASER PHOTOMIOSIS

RELATED APPLICATION

This application claimed priority to U.S. Provisional Application No. 61/603,281, filed Feb. 25, 2012, which application is incorporated by reference herein in its entirety.

TECHNICAL FIELD

The disclosed embodiments relate generally to systems and methods for treating disorders of the human eye, and specifically to a system method for improving vision using laser photomiosis.

BACKGROUND

Before the onset of presbyopia, the natural optical lens in the human eye has the ability to alter its focal length (e.g., to vary depth of field and focal plane) so as to focus objects at varying distances from the observer onto the observer's retina for visual interpretation by the observer's brain. With increasing age and the resulting onset of presbyopia, the eye lens progressively loses its ability to change focus and view with clarity objects that are outside a limited range of focus distances. This inability of the eye lens to change its focal length with age results in poor visual quality outside of a fixed focus distance. Additionally, lower and higher order aberrations (a common side effect of various types of refractive surgery) in the eye can lead to reduced visual quality, particularly in low illumination, which can present as symptoms of glare, halos, or reduced contrast sensitivity.

Current treatment methods for ameliorating the adverse effects of these losses in visual quality include short-term pharmacological treatment (e.g., the use of miotic agents) for losses in low light vision due to higher order aberrations as well as vision corrective surgeries that attempt to alter the focal distances of the human eye lens in order to improve the range of clear vision. The use of medical miotic agents is generally used only as a short-term solution due to decreasing efficacy and the potential for adverse side effects. Vision corrective surgeries have generally been found to be inadequate in reversing the effects of presbyopia that occur with age.

SUMMARY

Disclosed are methods and systems for improving near visual acuity by reducing defocus blur in patients with presbyopia and also improving visual performance in individuals with visual symptoms caused by aberrations (including higher order aberrations), particularly those caused by refractive surgery. The methods and systems described realize these improvements without altering the natural focusing capability of the human eye through surgical intervention (such as by treatments to the lens or ciliary muscle) and without the need for long-term medical treatment. As such, the disclosed embodiments address the need for improving visual acuity in patients with presbyopia by permanently decreasing the diameter of the patient's pupils by cauterizing (e.g., heating and/or treating using a laser light beam) specific iris tissues in specific predetermined patterns so as to reduce the ability of the iris to dilate the pupil. The disclosed approaches of reducing the pupil's diameter result in a reduction of defocus blur and visual aberrations without the limitations of conventional approaches.

In accordance with some embodiments, a method of improving vision is performed by an ophthalmic laser system. The method includes obtaining a predetermined pattern characterized by a plurality of positions along a plurality of spatially distributed iris tissues of an eye of a patient. The method further includes aligning a laser illumination light beam in accordance with one or more of the plurality of positions along the plurality of spatially distributed iris tissues. The method also includes delivering the laser illumination light beam in the predetermined pattern to the desired location in the eye of the patient. The method further includes cauterizing (e.g., heating and/or treating) at least a subset of the spatially distributed iris tissues, by the delivery of the laser illumination light beam in the predetermined pattern, thereby resulting in a permanent decrease in diameter of the pupil of the eye.

DESCRIPTION OF EMBODIMENTS

It will also be understood that, although the terms "first," "second," etc. may be used herein to describe various elements, these elements should not be limited by these terms. These terms are only used to distinguish one element from another. For example, a first position could be termed a second position, and, similarly, a second position could be termed a first position, without changing the meaning of the description, no long as all occurrences of the "first position" are renamed consistently and all occurrences of the second position are renamed consistently. The first position and the second position are both position, but they are not the same position.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, hut do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Reference will now be made in detail to various embodiments, examples of which are illustrated in the accompanying drawings. In the following detailed description, numerous specific details are set forth in order to provide a thorough understanding of the invention and the described embodiments. However, the invention may be practiced without these specific details. In other instances, well-known methods, procedures, components, and circuits have not been described in detail so as not to unnecessarily obscure aspects of the embodiments.

Figure 1:
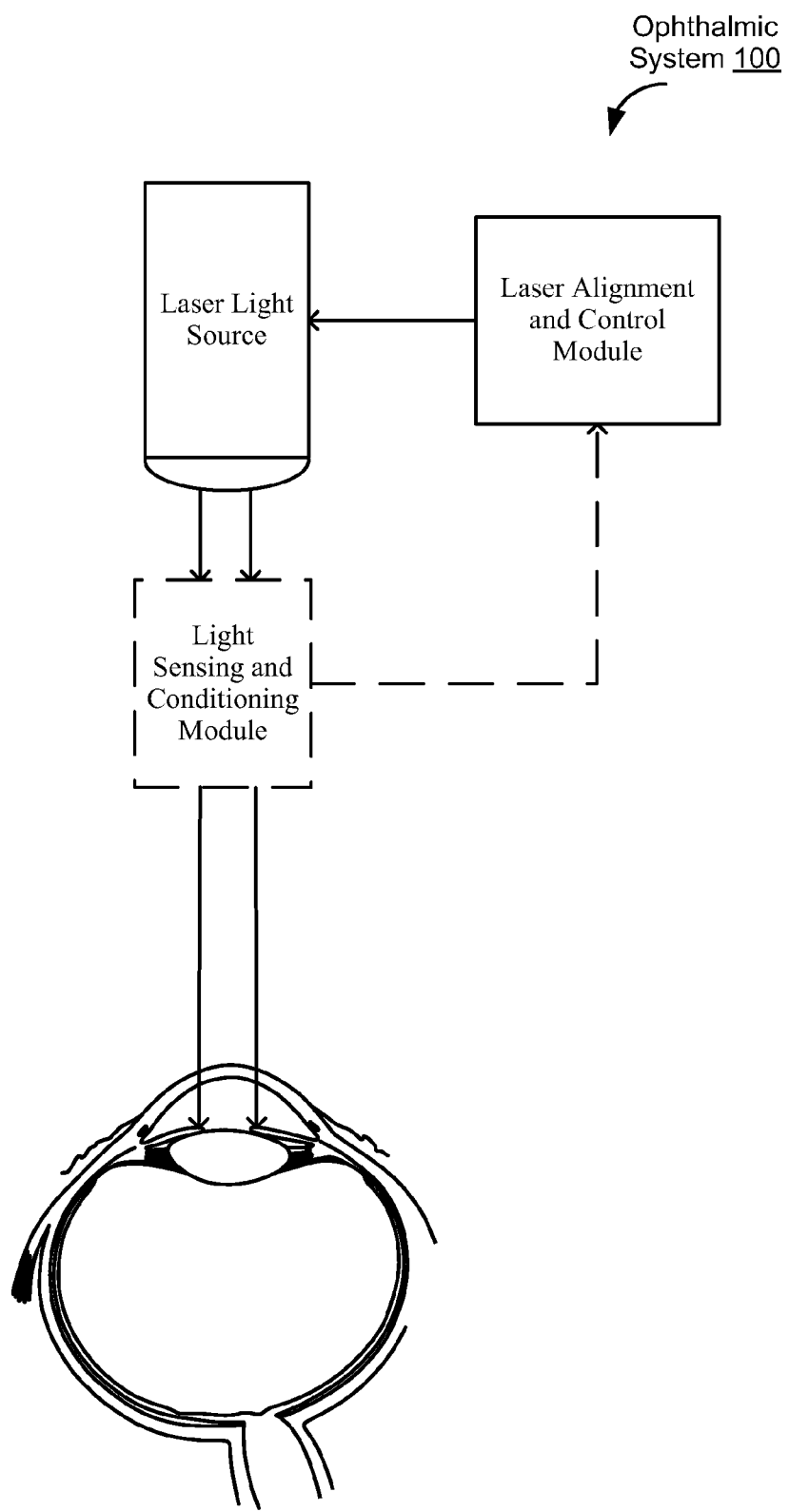
FIG. 1 includes a block diagram of an ophthalmic laser system, in accordance with some embodiments of this disclosure.

FIG. 1 includes a block diagram of an ophthalmological laser system 100, in accordance with some embodiments of this disclosure.

As shown in FIG. 1, ophthalmological laser system 100 comprises a laser light source 102, a laser alignment and control module 104, and optionally a light sensing and conditioning module 106. The radiation of laser light source 102 is focusable as a laser illumination light beam 108.

Ophthalmological laser system 100 includes at least one processor (e.g., in laser alignment and control module 104, in light sensing and conditioning module 106, or separately from both or within both); memory (e.g., in laser alignment and control module 104, in light sensing and conditioning module 106, separately from both or within both); and at least one program stored in the memory and executable by the at least one processor, the at least one program comprising instructions to perform one or more operations for improving vision at ophthalmological laser system 100.

The one or more operations include obtaining a predetermined pattern characterized by a plurality of positions along a plurality of spatially distributed iris tissues of an eye of a patient. Accordingly, in some embodiments, the ophthalmological laser system 100 (e.g., the laser alignment and control module 104) retrieves (e.g., stored in memory) or generates a predetermined pattern including a plurality of positions along which the laser light beam from laser light source 102 is targeted on the patient's iris (for example, as explained with reference to FIGS. 4A-4B, 5A-5B, 6A-6B, 7, 8, and 9 below). The plurality of positions occurs along spatially distributed iris tissues of the eye of the patient (e.g., the plurality of positions and the predetermined pattern).

The one or more operations include aligning the laser illumination light beam in accordance with one or more of the plurality of positions along a plurality of spatially distributed iris tissues. In some embodiments, the optional light sensing and conditioning module 106 determines parameters specific to the patient that determine or guide the alignment of the laser light beam onto the patient's iris tissues. In such embodiments, the light sensing and conditioning module 106 determines (e.g., measures and/or estimates) an individual patient's eye size, iris diameter, tissue transparency, extent of pupil dilation, distance or the eye and/or iris tissue to laser light source and the like. The light sensing and conditioning module 106 optionally provides a feedback signal to the laser alignment and control module 101 so as to guide the alignment of the laser illumination light beam in accordance with one or more of the plurality of positions along a plurality of spatially distributed iris tissues on the patient's iris based on the patient-specific parameters determined by the light sensing and conditioning module 106. The light sensing and conditioning module 106 optionally focuses and guides the optical path of the laser light beam 108 onto one or more of the plurality of positions along a plurality of spatially distributed iris tissues.

The one or more operations further include delivering the laser illumination light beam 108 in the predetermined pattern on a surface of the eye of the patient; and cauterize (e.g., treating and/or heating to a predetermined temperature) at least a subset of the spatially distributed iris tissues, by the delivery of the laser illumination light beam 108 in the predetermined pattern, causing the subset of iris tissues to scarify thereby resulting in a permanent decrease in diameter of the pupil of the eye. In some embodiments, by weakening or scarifying specific muscles (e.g., the dilator muscles) in the patient's iris, the capacity or ability of the respective muscles to contract is reduced causing the muscles to be limited in their ability to shorten in length (or contract).

In some embodiments, the laser light source 102 is a pulse laser and the laser illumination light beam 108 comprises a sequence of light pulses of average time duration between 100 femtoseconds and 100 milliseconds.

In some embodiments, the laser light source 102 is a pulse laser and the laser illumination light beam 108 comprises a sequence of a plurality of light pulses with an average repetition rate between consecutive light pulses in the plurality of light pulses that is between 2 Hertz and 100 kiloHertz. In some embodiments, a slower laser (e.g., a laser with a lower pulse repetition rate) is used to target the inner iris or the stromal tissue and heat the tissue to cause contraction of the collagen in the stroma; when targeted on the dilator muscles, the slower laser causes weakening of the dilator muscles. In some embodiments, a faster laser (e.g., a laser with a higher pulse repetition rate, for example, used in conjunction with the predetermined pattern shown in FIGS. 4A-4B) is used to target a substantial portion of the length of the iris to cut (e.g., to scarify) the collagen in the stromal tissue.

In some embodiments, the laser illumination light beam 108 comprises laser light of wavelength between 530 nanometers and 1700 nanometers.

Figure 2A:
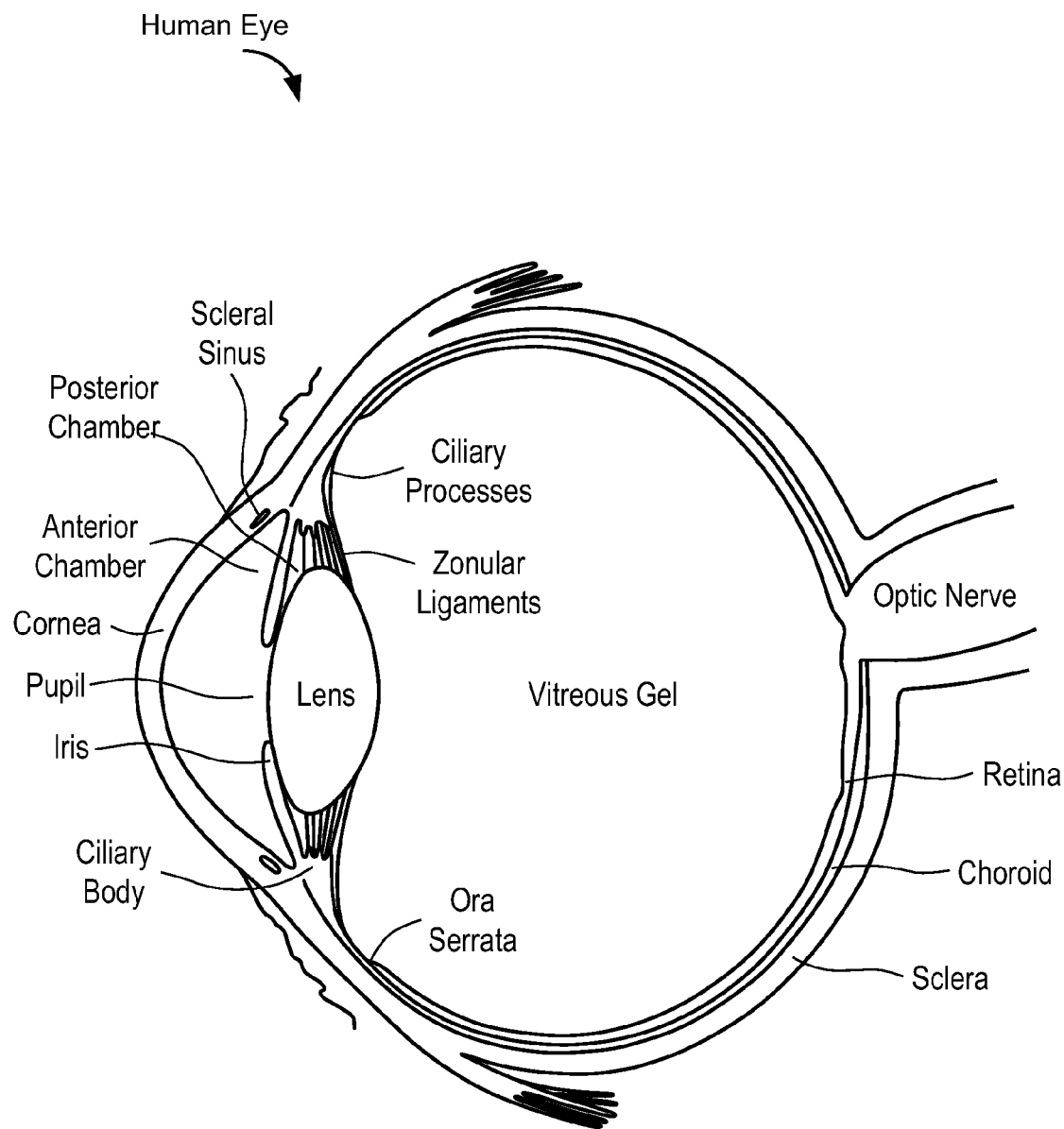
FIG. 2A illustrates a cross-sectional anatomical view of a human eye in accordance with the prior art.

In some embodiments, one or more laser parameters are obtained in accordance with the obtained predetermined pattern. In some embodiments, for one or more of a wavelength of laser light beam, a pulse repetition rate of pulses of the laser light beam, a pulse duration of the pulses of the laser light beam, a duration of treatment of the spatially distributed iris tissues is different for the substantially radial predetermined pattern (e.g., as described further with reference to FIGS. 4A-4B) compared to the substantially circumferential predetermined pattern (e.g., as described further with reference to FIGS. 5A-5B), and is different for the substantially circular predetermined spot treatment pattern (e.g., as described further with reference to FIG. 8). In some embodiments, a combination of laser parameters are used to achieve a predetermined pattern characterized by a respective combination of one or more of a substantially radial predetermined pattern, a substantially circumferential predetermined pattern, and a substantially circular predetermined spot treatment pattern (e.g., as described with reference to FIG. 7 and FIG. 9). In some embodiments, the predetermined pattern is a closed shape around the iris. Examples, of such closed shapes include, but are not limited to, a respective combination of one or more of a substantially radial predetermined pattern, a substantially circumferential predetermined pattern, and a substantially circular predetermined spot treatment pattern. However, the present disclosure is not so limited. In sonic embodiments, the predetermined pattern is an open shape around the iris, meaning that, in such embodiments, the predetermined pattern does not reach all the way around the eye with respect to the iris. In fact, in some embodiments, the shape traverses less than 90 percent, less than 80 percent, less than 70 percent, less than 60 percent, less than 50 percent, or less than 40 percent around the eye with respect to the pupil. In such embodiments, the predetermined pattern is a substantially radial predetermined pattern, a substantially circumferential predetermined pattern, and a substantially circular predetermined spot treatment pattern that traverses less than 90 percent, less than 80 percent, less than 70 percent, less than 60 percent, less than 50 percent, or less than 40 percent around the eye with respect to the pupil. In some embodiments, the predetermined pattern, while being a respective combination of one or more of a substantially radial predetermined pattern, a substantially circumferential predetermined pattern, and a substantially circular predetermined spot treatment pattern, does not cover one, two, three, four, five, six, seven, or eight or more portions of the eye radiating from the pupil. FIG. 2A illustrates a cross-sectional anatomical view of a human eye. As shown in FIG. 2A, the human eye has three layers: the sclera and cornea; the iris (on the anterior side) and the choroid (posterior); and the retina. The iris is the colored annular portion of the eye visible in the frontal view. The pupil is the dark opening in the center of the iris that permits light to enter the posterior regions of the eye. The size of the pupil opening determines the intensity of light entering the eye. The size of the pupil opening is governed by the extent of contraction of the iris muscles as explained below with reference to FIGS. 2B-2C. The eye lens focuses the light entering through the pupil through a process known as "accommodation" by way of changing the focal length of the lens via the ciliary muscles. Vision defects (e.g., near-sightedness or myopia; or far-sightedness or hypermetropia; or presbyopia) are frequently corrected by the use of one or more external lenses for augmenting the eye's natural ability to focus the incoming light onto the retina or by altering or modifying the eye's natural "accommodation" function by targeting the ciliary muscles or the eye's natural lens.

Alternatively, vision improvement methods that do not affect "accommodation" presented here are targeted toward reducing the pupil's ability to dilate, by affecting the iris tissues that impact the extent of pupil opening. Such methods of vision correction prevent peripheral and stray light from entering the pupil thereby reducing optical aberrations and improving visual acuity without impacting the eye's natural "accommodation." The disclosed methods would help increase the depth of focus for patient's presenting with presbyopia without impacting the functioning of the natural eye lens (e.g., without impacting the eye's natural "accommodation" process). As a result, the disclosed embodiments would help improve visual acuity at near distances in patients presenting with presbyopia.

In some embodiments an ophthalmological laser system comprises a laser, the radiation of which is focusable as a laser illumination light beam forming a predetermined pattern characterized by a plurality of positions along a plurality of spatially distributed iris tissues of an eye of a patient. The ophthalmological laser system further comprises an alignment mechanism for aligning said laser illumination light beam in accordance with one or more of the plurality of positions along the plurality of spatially distributed iris tissues. The ophthalmological laser system also comprises a delivery mechanism for delivering said laser illumination light beam in the predetermined pattern on a surface of the eye of the patient thereby cauterizing at least a subset of the spatially distributed iris tissues, by the delivery of the laser illumination light beam in the predetermined pattern, thereby resulting in a permanent decrease in diameter of the pupil of the eye. In some embodiments, the laser is a vertical-cavity emitting surface-emitting laser. In some embodiments, the laser is a continuous wave laser that is pulsed.

In some embodiments, an optical amplification system comprises an optical amplifier, the emission of which is focusable as an emission beam forming a predetermined pattern characterized by a plurality of positions along a plurality of spatially distributed iris tissues of an eye of a patient. The optical amplification system further comprises an alignment mechanism for aligning said emission beam in accordance with one or more of the plurality of positions along the plurality of spatially distributed iris tissues. The optical amplification system further comprises a delivery mechanism for delivering said emission beam in the predetermined pattern on a surface of the eye of the patient thereby cauterizing at least a subset of the spatially distributed iris tissues, by the delivery of the emission beam in the predetermined pattern, thereby resulting in a permanent decrease in diameter of the pupil of the eye. In some embodiments, the optical amplifier is a laser or photon generator.

In some embodiments, an optical amplification system comprises an optical Amplifier, the emission of which is focusable as an emission beam. The optical amplification system further comprises at least one processor, memory, and at least one program stored in the memory and executable by the at least one processor, the at least one program comprising instructions to: obtain a predetermined pattern characterized by a plurality of positions along a plurality of spatially distributed iris tissues of an eye of a patient; align said emission beam in accordance with one or more of the plurality of positions along the plurality of spatially distributed iris tissues; deliver said emission beam in the predetermined pattern on a surface of the eye of the patient; and cauterize at least a subset of the spatially distributed iris tissues, by the delivery of the emission beam in the predetermined pattern, thereby resulting in a permanent decrease in diameter of the pupil of the eye.

In some embodiments, an acoustic amplification system comprises an acoustic amplifier, the emission of which is focusable as an emission beam forming a predetermined pattern characterized by a plurality of positions along a plurality of spatially distributed iris tissues of an eye of a patient. The acoustic amplification system further comprises an alignment mechanism for aligning said emission beam in accordance with one or more of the plurality of positions along the plurality of spatially distributed iris tissues; and a delivery mechanism for delivering said emission beam in the predetermined pattern on a surface of the eye of the patient thereby cauterizing at least a subset of the spatially distributed iris tissues, by the delivery of the emission beam in the predetermined pattern, thereby resulting in a permanent decrease in diameter of the pupil of the eye. In some embodiments, the acoustic amplifier is an ultrasound energy generator.

In some embodiments, an acoustic amplification system comprises an acoustic amplifier, the emission of which is focusable as an emission beam; at least one processor; memory; at least one program stored in the memory and executable by the at least one processor, the at least one program comprising instructions to: obtain a predetermined pattern characterized by a plurality of positions along a plurality of spatially distributed iris tissues of an eye of a patient; align said emission beam in accordance with one or more of the plurality of positions along the plurality of spatially distributed iris tissues; deliver said emission beam in the predetermined pattern on a surface of the eye of the patient; and cauterize at least a subset of the spatially distributed iris tissues, by the delivery of the emission beam in the predetermined pattern, thereby resulting in a permanent decrease in diameter of the pupil of the eye.

It will be understood that one or more of the systems disclosed herein (e.g., the ophthalmic laser system, the ophthalmological laser system, the optical amplification system, the acoustic amplification system, and the like) are optionally fabricated to include one or more of the predetermined patterns (e.g., rather than obtaining the predetermined patterns from memory). Alternatively, or in addition, one or more of the systems described herein are configured to retrieve one or more of the predetermined patterns from memory or generate one or more of the predetermined patterns.

Figure 2B:
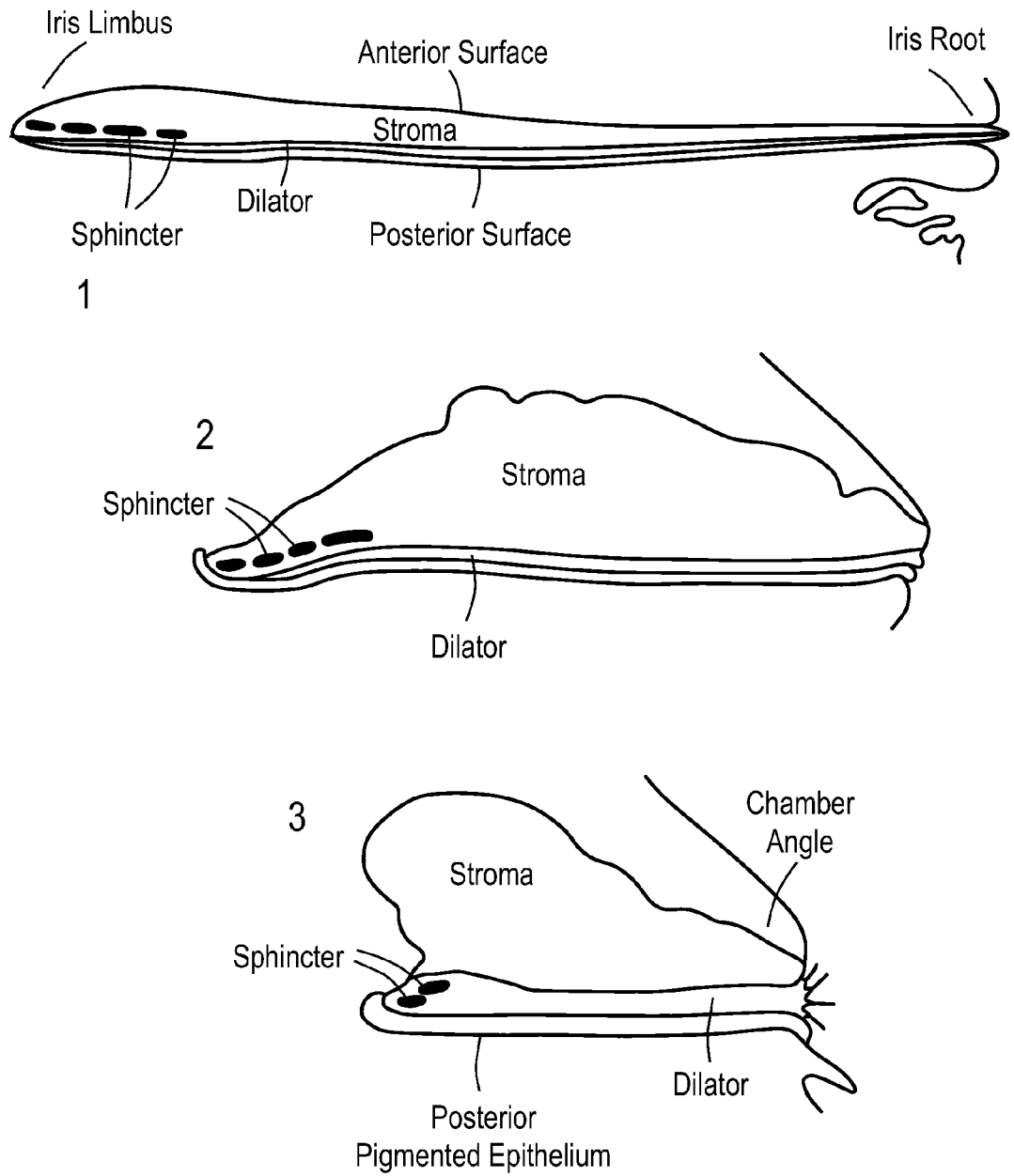
FIG. 2B illustrates cross-sectional views of a human iris with various lengths (e.g., extents of contraction of iris muscles), thereby causing various extents of pupil dilation in accordance with the prior art.
Figure 2C:
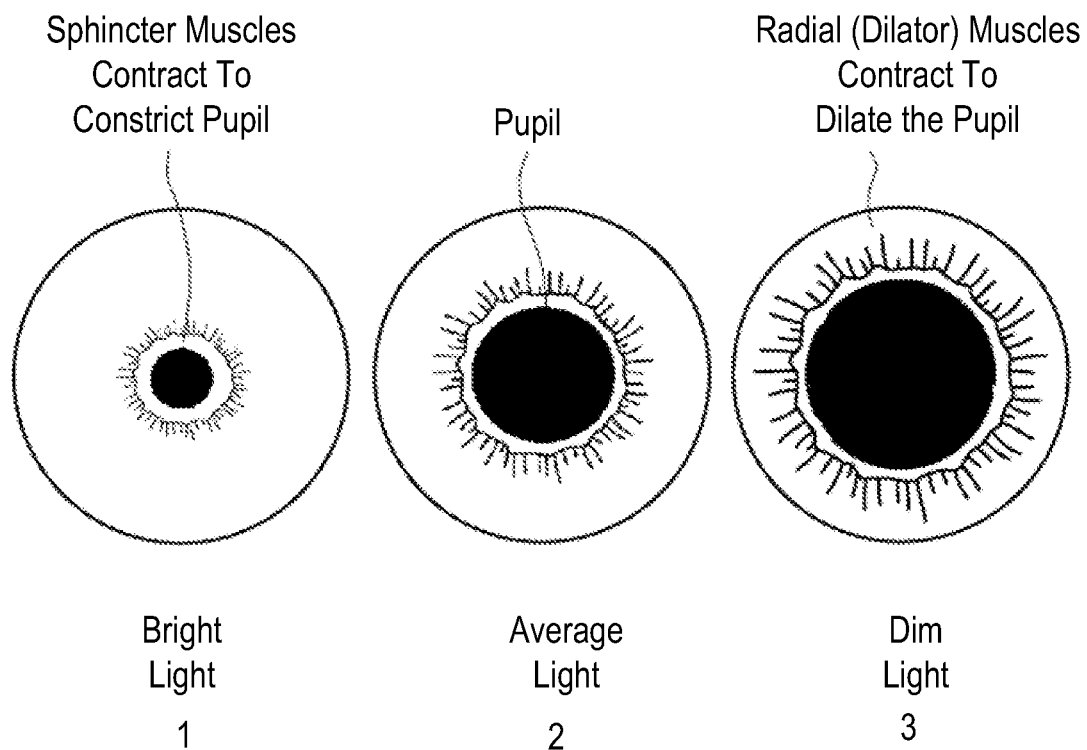
FIG. 2C illustrates frontal views of a human iris with various extents of contraction of iris muscles, thereby causing various extents of pupil dilation (e.g., in response to intensity of ambient light) in accordance with the prior art.

FIG. 2B illustrates cross-sectional views of a human iris through various lengths and extents of contraction of iris muscles, thereby causing various extents of pupil dilation. FIG. 2C illustrates frontal views of a human iris through various lengths and extents of contraction of iris muscles, thereby causing various extents of pupil dilation (e.g., in response to ambient light conditions).

As explained in FIG. 1, ophthalmological system 100 focuses laser light beam 108 (FIG. 1) onto a plurality of spatially distributed iris tissues of the patients eye. In some embodiments, the plurality of spatially distributed iris tissues includes one of the iris stromal tissue (as shown in FIG. 2B), the iris dilator muscle tissue (FIG. 2B-2C), the iris limbus tissue (FIG. 2B), or any combination thereof.

In some embodiments, the predetermined pattern (e.g., of the one or more of the plurality of positions along a plurality of spatially distributed iris tissues) includes a substantially radial pattern. In such embodiments, the laser light beam is focused on and cauterizes (e.g., heats, scarifies and/or cuts) the iris stromal tissue and/or the iris dilator muscle tissue. In some embodiments, to produce contraction of the collagen in the stroma, the stroma is targeted with the laser light beam. In some embodiments, to cause a weakening of the dilator muscle, the dilator muscle is cut with or affected by the laser light beam.

In some embodiments, the predetermined pattern (e.g., of the one or more of the plurality of positions along a plurality of spatially distributed iris tissues) includes a substantially circumferential pattern. In some embodiments, the circumferential pattern is defined or formed along (e.g., proximal to) the inner circumference of the iris (e.g., external and adjacent to the sphincter muscle, for example targeting the iris stromal tissue and the iris dilator muscles). In such embodiments, the laser light beam is focused on, and cauterizes (e.g., heats, cuts, and/or scarifies) the iris tissue (e.g., near the iris limbus or the tissue external and adjacent to the sphincter muscle, for example targeting the iris stromal tissue and the iris dilator muscles). In some embodiments, the circumferential pattern is defined or formed along (e.g., proximal to) the outer circumference of the iris (e.g., near the iris root). In such embodiments, the laser light beam is focused on, and cauterizes (e.g., heats, cuts and/or scarifies) the iris dilator muscle tissue. In some embodiments, the circumferential pattern is any closed form pattern, or substantially closed form pattern, that includes an arcuate edge and defines two or more, three or more, four or more, five or more, or six or more positions about the pattern where a cut is to be made by a laser or other cutting instrument, such as a surgical tool.

In some embodiments, the predetermined pattern (e.g., of the one or more of the plurality of positions along a plurality of spatially distributed iris tissues) includes a substantially circular spot pattern. In some embodiments, the substantially circular spot pattern is formed along (e.g., proximal to) the inner circumference of the iris (e.g., external and adjacent to the sphincter muscle, for example targeting the iris stromal tissue and the iris dilator muscles). In such embodiments, the laser light beam is focused on, and cauterizes (e.g., heats, cuts, and/or scarifies) the iris tissue (e.g., near the iris limbus or the tissue external and adjacent to the sphincter muscle, for example targeting the iris stromal tissue and the iris dilator muscles).

In some embodiments, the predetermined pattern (e.g., of the one or more of the plurality of positions along a plurality of spatially distributed iris tissues) includes a combination of two or inure of a substantially radial pattern, a substantially circumferential pattern, and a substantially circular spot pattern. In such embodiments, the laser light beam is focused on, and cauterizes (e.g., heats, cuts, and/or scarifies) one or more of: the iris dilator muscle tissue, the iris limbus tissue (e.g., external and adjacent to the sphincter muscle, for example targeting the iris stromal tissue and the iris dilator muscles), and the iris stromal tissue.

It will be understood that FIG. 1 and FIGS. 2A-2C are merely representative and illustrative and are not meant to be anatomically accurate representations of the human eye or parts thereof.

Figure 3:
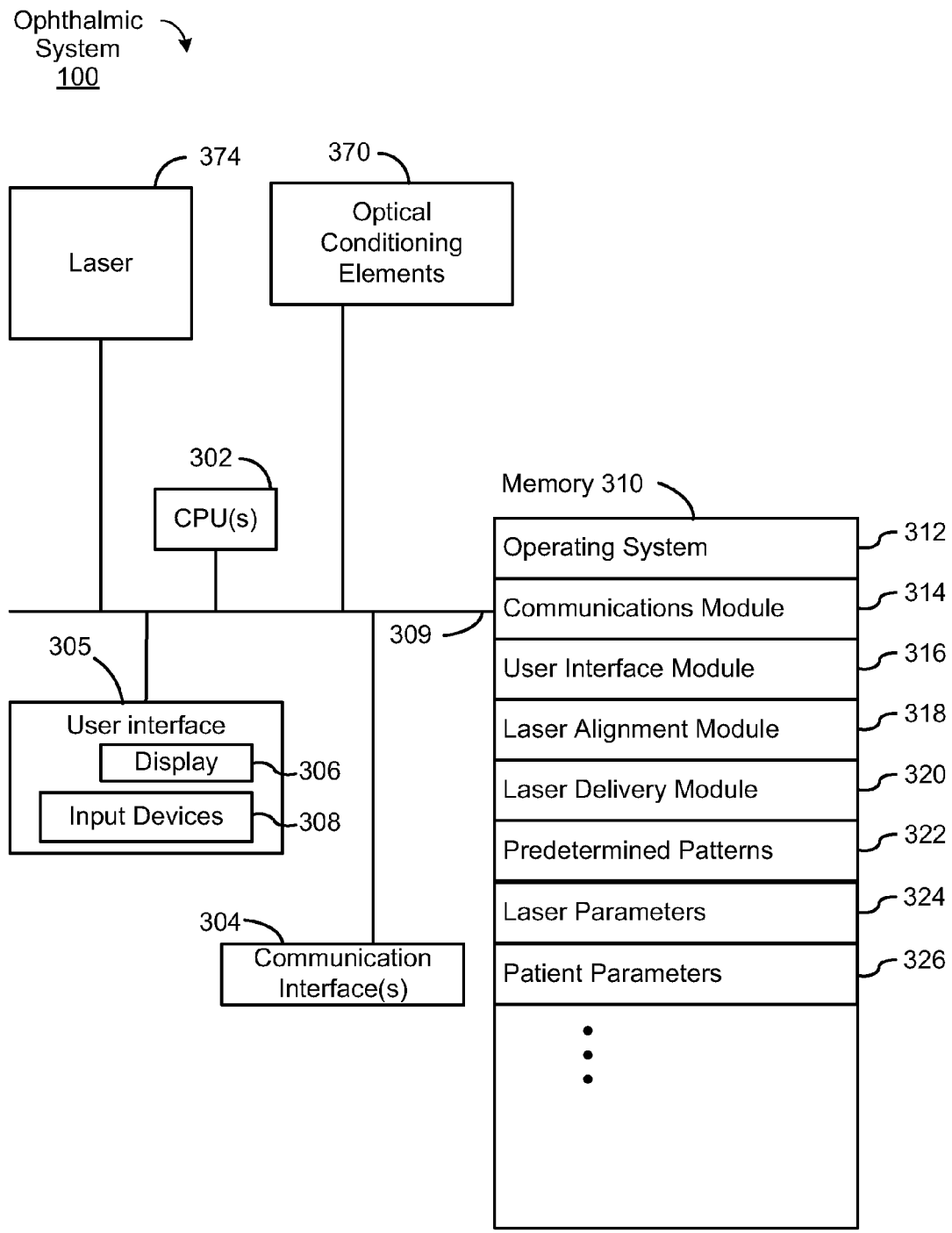
FIG. 3 is a block diagram illustrating an ophthalmic laser system, in accordance with some embodiments of the present disclosure.

FIG. 3 is a block diagram illustrating an ophthalmic laser system 100 in accordance with one embodiment of the present invention. The ophthalmic laser system 100 typically includes one or more processing units (CPU's) 302 for executing modules, programs and/or instructions stored in memory 310 and thereby performing processing operations; one or more network or other communications interfaces 304; memory 310; and one or more communication buses 314 for interconnecting these components. The communication buses 309 optionally include circuitry (sometimes called a chipset) that interconnects and controls communications between system components. The ophthalmic laser system 100 optionally may include a user interface 305 comprising a display device 306 and an input device 308. Laser 374 includes one or more discrete laser light sources (e.g., with one or more wavelengths of pulse laser output) that is used to generate the laser light beam directed onto the surface of the patient's iris. Optical conditioning elements 370 optionally include optical assembly and components to focus, align, and condition the laser light beam generated by laser 371. Memory 310 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 310 may optionally include one or more storage devices remotely located from the CPU(s) 302. Memory 310, or alternately the non-volatile memory device(s) within memory 310, comprises a non-transitory computer readable storage medium. In some embodiments, memory 310, or the computer readable storage medium of memory 310 stores the following programs, modules and data structures, or a subset thereof:

- an operating system 312 that includes procedures for handling various basic system services and for performing hardware dependent tasks;
- a network communication module 311 that is used for connecting the ophthalmic laser system 100 to other computers via the one or more communication network interfaces 309 (wired or wireless) and one or more communication networks, such as the Internet, other wide area networks, local area networks, metropolitan area networks, and so on;
- a user interface module 316 that receives commands from the user via one or more input devices 308 of user interface 305, generates user interface objects in display device 306, and/or a visual representation of the patient's iris or other parts of the patient's eye, a representation of one or more of the predetermined patterns superimposed on the visual representation of the patient's iris. The user interface module 316 optionally facilitates the alignment of laser light beam on specific portions of the patient's iris;
- a laser alignment module 318 that provides commands to align a laser light beam in accordance with a selected predetermined pattern and optionally guides the laser light beam along the plurality of positions along the spatially distributed iris tissues that characterize the predetermined pattern;
- a laser delivery module 320 that includes control instructions and commands to operate laser 374 to produce laser light beam that is optionally directed through optical conditioning elements 370 to be incident on the patient's iris;
- predetermined patterns 322 that include multiple sets of predetermined patterns (stored, for example, in a database of predetermined patterns) that correspond to a plurality of positions along a plurality of spatially distributed iris tissues along which the laser beam is aligned (e.g., by the laser alignment module 318) for vision treatment or vision improvement;
- laser parameters 324 are sets of parameters (e.g., wavelength of laser light, average pulse duration, average pulse repetition rate, average treatment time, average treatment temperature or range of temperature increase of tissue, laser peak power, laser pulse energy, and the like) are optionally selected in accordance with the selected predetermined pattern from the predetermined patterns 322 for vision treatment or vision improvement; and
- patient parameters 326 are sets of parameters (e.g., iris dimensions—inner and outer circumferences of the iris and iris thickness, extent of pupil dilation, pupil diameter, distance of treatment area from the laser source, and the like) that are specific to individual patients and are optionally used to determine the predetermined pattern and the laser parameter used for vision treatment or vision improvement.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, memory 310 may store a subset of the modules and data structures identified above. Furthermore, memory 310 may store additional modules and data structures not described above.

Although FIG. 3 shows an "ophthalmological laser system," FIG. 3 is intended more as functional description of the various features which may be present in a set of servers than as a structural schematic of the embodiments described herein. In practice, and as recognized by those of ordinary skill in the art, items shown separately could be combined and some items could be separated. For example, some items shown separately in FIG. 3 could be implemented on single servers and single items could be implemented by one or more servers. The actual number of servers used to implement an ophthalmological laser system and how features are allocated among them will vary from one implementation to another.

Figure 4A:
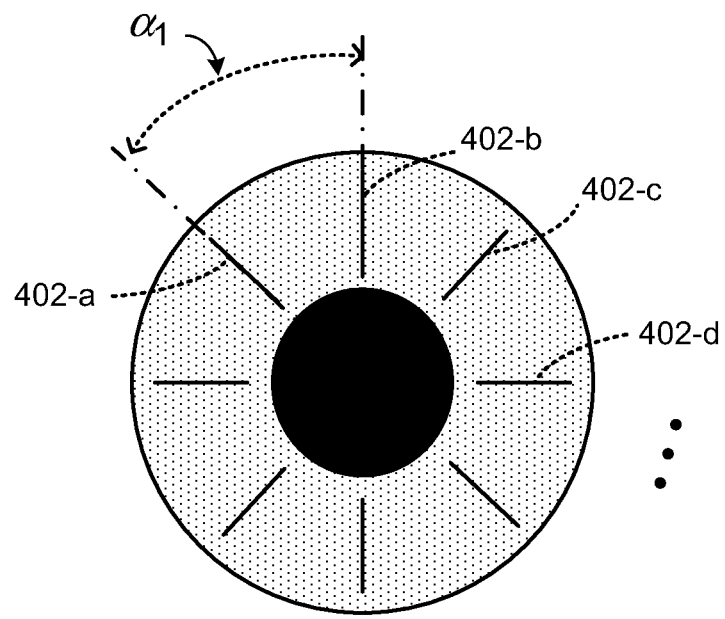
FIG. 4A-4B illustrate substantially radial predetermined patterns of positions for delivering the laser light beam on one or more of the iris tissues of a patient's eye, in accordance with some embodiments of the present disclosure.
Figure 4B:
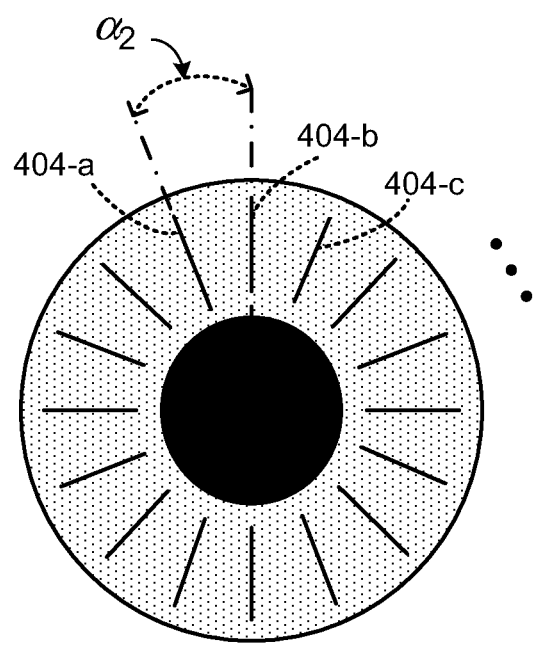

FIGS. 4A-4B illustrate substantially radial predetermined patterns of positions for delivering the laser light beam on one or more of the iris tissues of a patient's eye, in accordance with some embodiments of the present disclosure.

Accordingly, in some embodiments, the predetermined pattern is a substantially radial pattern. The plurality of positions comprises N positions (e.g., positions 402-1, 402-b, 402-c, and the like where N=8 as shown in FIG. 4A; positions 404.1, 404-b, 404-c, and the like where N=16 as shown FIG. 4B), each of the N positions oriented radially from the inner circumference (e.g., from the iris limbus; external and adjacent to the sphincter muscle, for example targeting the iris stromal tissue and/or the iris dilator muscles, as explained with reference to FIG. 2B) of the iris proximal to the pupil to the outer circumference (e.g., the iris root, as explained with reference to FIG. 2B) of the iris distal to the pupil. The N positions include a first position (e.g., position 402-a, FIG. 4A; position 404-a, FIG. 4B) and a second position (e.g., position 402-b, FIG. 4A; position 404-b, FIG. 4B) adjacent to the first position and separated from the first position by a predefined angular separation (e.g., positions 402-a and 402-b are separated by the predefined angular separation $\alpha_1$ of approximately 45° as shown in FIG. 4A; positions 404-a and 404-b are separated by the predefined angular separation $\alpha_2$ of approximately 22.5° as shown in FIG. 4B). In some embodiments, each position of the plurality of positions corresponds to a treatment zone (e.g., a cut) on the patient's iris using the laser light beam.

In some embodiments, the predefined angular separation has a value between 10° and 50° and N is a positive integer of value between 4 and 36. In some embodiments, an average length of the plurality of positions (e.g., or cuts or treatment zones) has a value between 1 mm and 3 mm. In some embodiments, an average thickness of the plurality of positions (e.g., or cuts or treatment zones) has a value between 10 microns and 200 microns. In some embodiments, the laser light beam is focused on the plurality of positions, thereby causing scarification of the iris stromal tissue.

Figure 5A:
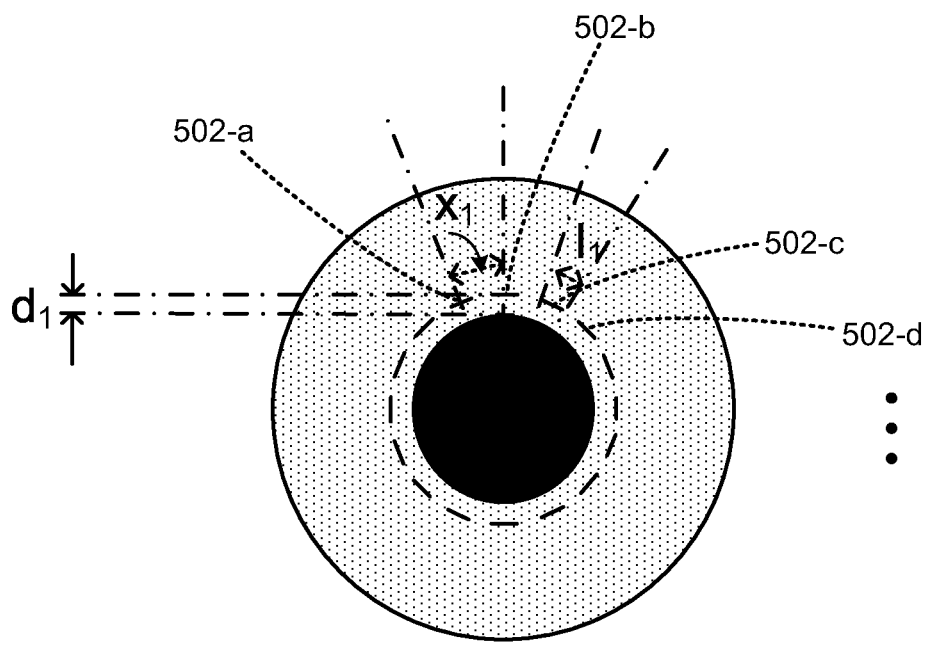
FIG. 5A-5B illustrate substantially circumferential predetermined patterns of positions for delivering the laser light beam on one or more of the iris tissues of a patient's eye, in accordance with some embodiments of the present disclosure.
Figure 5B:
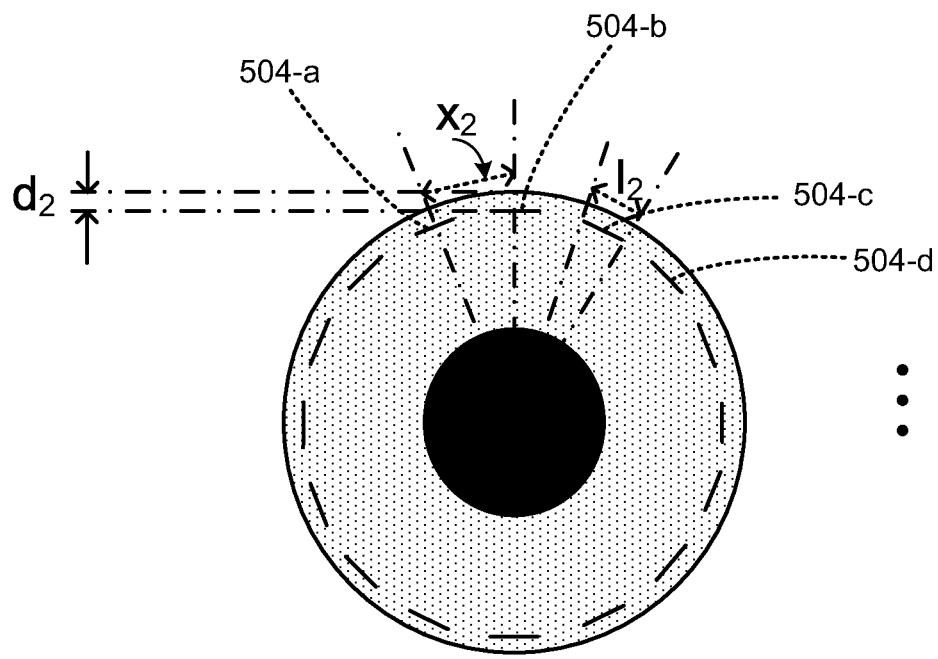

FIGS. 5A-5B illustrate substantially circumferential predetermined patterns of positions for delivering the laser light beam on one or more of the iris tissues of a patient's eye, in accordance with some embodiments of the present disclosure.

As shown in FIG. 5A, the substantially circumferential pattern is formed proximal to the inner circumference of the iris. In some embodiments, the predetermined pattern is a substantially circumferential pattern. The plurality of positions comprises N positions (e.g., positions 502-1, 502-b, 502-c, and the like where N=16 as shown in FIG. 5A), each of the N positions occurring at a first predetermined distance (e.g., distance $d_1$ as shown in FIG. 5A) along a radius of the iris measured from the inner circumference of the iris. The N positions together form the substantially circumferential pattern which is substantially concentric with and proximal to the inner circumference of the iris (e.g., proximal to the iris limbus; external and adjacent to the sphincter muscle, for example targeting the iris stromal tissue and/or the iris dilator muscles, as explained with reference to FIG. 2B). The N positions include a first position (e.g., position 502-a, FIG. 5A) and a second position (e.g., position 502-b, FIG. 5B) adjacent to the first position, wherein a center of the first position is separated from a center of the second position by a predetermined separation (e.g., separation $x_1$ as shown in FIG. 5A) along the circumferential pattern. In some embodiments, each position of the plurality of positions corresponds to a treatment zone (e.g., a cut) on the patient's iris using the laser light beam. It will be appreciated that a certain amount of variation in the distance of each of the positions from the iris as measured from the center of the pupil may be incurred when using the predetermined patterns and that such variations are within the scope of the present disclosure. In some instances, such variation is intentional, in some instances such variation is due to imperfections in the symmetry of features of the subject eye, and in some instances such variation arises due to the precision or accuracy of the apparatus applying cuts to the eye. In some instance, such variation arises to any combination of the above-identified factors or for other reasons.

In some embodiments, the first predetermined distance has a value between 0.75 millimeters and 1.5 millimeters, the predetermined separation has a value between 50 micrometers and 300 micrometers, an average length of the first position (e.g., length $l_1$ of position 502-c, FIG. 5A) has a value between 25 micrometers and 200 micrometers, and N is a positive integer of value between 4 and 20. In some embodiments, the laser light beam is focused on the plurality of positions, thereby causing weakening of dilator muscle and scarification of posterior stroma.

In some embodiments, for the predetermined pattern described with reference to FIG. 5A, a wavelength of the laser light beam has a value between 500 nanometers and 1100 nanometers. In some embodiments, a wavelength of the laser light beam has a value between 532 nanometers and 1064 nanometers.

In some embodiments, for the predetermined pattern described with reference to FIG. 5A, the laser light source is a pulse laser and an average duration of laser pulses has a value between 0.1 milliseconds and 20 milliseconds. In some embodiments, an average duration of laser pulses has a value between 0.5 milliseconds and 2 milliseconds.

In some embodiments, for the predetermined pattern described with reference to FIG. 5A, the laser light source is a pulse laser and an average repetition rate (e.g., frequency of repetition or pulsing) of laser pulses has a value between 0.5 Hertz and 800 Hertz. In some embodiments, an average repetition rate (e.g., frequency of repetition or pulsing) of laser pulses has a value between 20 Hertz and 60 Hertz.

In some embodiments, for the predetermined pattern described with reference to FIG. 5A, the laser light source is a pulse laser and the laser peak power has a value between 5 milliWatts and 1000 milliWatts. In some embodiments, the laser peak power has value of between 100 milliWatts and 300 milliWatts.

In some embodiments, for the predetermined pattern described with reference to FIG. 5A, the laser light source is a pulse laser with an average laser pulse energy having a value between 5 microJoules and 7500 microJoules. In some embodiments, the average laser pulse energy has a value between 200 microJoules and 1000 microJoules.

In some embodiments, for the predetermined pattern described with reference to FIG. 5A, an average laser power has a value between 1 milliWatt and 500 milliWatts. In some embodiments, the average laser power is between 10 milliWatts and 50 milliWatts.

Additional examples of laser parameters and operating conditions and ranges, that are used in some embodiments of the present disclosure are as described below:
- Number of laser-machined features between 100 and 25,000, (e.g., between 1000-5000);
- Diameter of posterior iris individual laser feature between 30 micrometers and 300 micrometers (e.g., diameter between 25 micrometers and 100 micrometers);
- Feature thickness between 50 micrometers and 200 micrometers e.g., between 75 micrometers and 125 micrometers);
- Fraction of iris area treated between 1% and 20% (e.g., about 5%);
- Clinical laser exposure time between 20 seconds and 100 seconds (e.g., between 30-60 seconds); and/or
- Focusing condition (e.g., spot size) between 0.3 and 0.6 NA (e.g., between 0.4-0.5 NA).

As shown in FIG. 5B, the substantially circumferential pattern is formed proximal to the outer circumference of the iris. In some embodiments, the predetermined pattern is a substantially circumferential pattern. The plurality of positions comprises N positions (e.g., positions 502-1, 502-b, 502-c, and the like where N=16 as shown in FIG. 5A), each of the N positions occurring at a second predetermined distance (e.g., distance $d_2$ as shown in FIG. 5B) along a radius of the iris measured from the outer circumference of the iris. The N positions together form the substantially circumferential pattern which is substantially concentric with and proximal to the outer circumference of the iris (e.g., the iris root, as explained with reference to FIG. 2B). The N positions include a first position (e.g., position 504-a, FIG. 5B) and a second position (e.g., position 504-b, FIG. 5B) adjacent to the first position, wherein a center of the first position is separated from a center of the second position by a predetermined separation (e.g., separation $x_2$ as shown in FIG. 5B) along the circumferential pattern. In some embodiments, each position of the plurality of positions corresponds to a treatment zone (e.g., a cut) on the patient's iris using the laser light beam.

In some embodiments, the second predetermined distance has a value between 0 and 1.5 millimeters, the predetermined separation has a value between 50 micrometers and 1 millimeter, an average length of the first position (e.g., length $l_2$ of position 504-c, FIG. 5B) has a value between 25 micrometers and 500 micrometers, and N is a positive integer of value between 4 and 20. In some embodiments, the laser light beam is focused on the plurality of positions, thereby causing weakening of dilator muscle and scarification of posterior stroma.

In some embodiments, for the predetermined pattern described with reference to FIG. 5B, a wavelength of the laser light beam has a value between 770 nanometers and 1700 nanometers. In some embodiments, a wavelength of the laser light beam has a value between 1000 nanometers and 1350 nanometers.

In some embodiments, the laser light beam is used for a first portion of the N positions of the predetermined pattern during a first session, and for a second portion of the N positions of the predetermined pattern during a second session at a time after the first session, where the time between the first session and the second session is more than five minutes, more than one hour more than one day, or more than one week.

In some embodiments, the laser light beam is used for each of the N positions of the predetermined pattern during a first session, and for all or a portion of the N positions of the predetermined pattern during a second session at a time after the first session, where the time between the first session and the second session is more than five minutes, more than one hour more than one day, or more than one week.

In some embodiments, the laser light beam is used for a portion of the N positions of the predetermined pattern during a first session, and for all or a portion of the N positions of the predetermined pattern during a second session at a time after the first session, where the time between the first session and the second session is more than five minutes, more than one hour more than one day, or more than one week.

In some embodiments, for the predetermined pattern described with reference to FIG. 5B, the laser light source is a pulse laser and an average duration of laser pulses has a value between 100 femtoseconds and 1000 femtoseconds. In some embodiments, an average duration of laser pulses has a value between 150 femtoseconds and 600 femtoseconds.

In some embodiments, for the predetermined pattern described with reference to FIG. 5B, the laser light source is a pulse laser and an average repetition rate (e.g., frequency of repetition or pulsing) of laser pulses has a value between 1 kiloHertz and 100 kiloHertzs. In some embodiments, an average repetition rate (e.g., frequency of repetition or pulsing) of laser pulses has a value between 10 kiloHertzs and 25 kiloHertzs.

In some embodiments, for the predetermined pattern described with reference to FIG. 5B, the laser light source is a pulse laser and an average laser peak power has a value between 10 Mega Watts and 1000 Mega Watts. In some embodiments, the average laser peak power has value of 100 MWs.

In some embodiments, for the predetermined pattern described with reference to FIG. 5B, the laser light source is a pulse laser and an average laser pulse energy has a value between 5 microJoules and 100 microJoules. In some embodiments, an average laser pulse energy has a value between 10 microJoules and 50 microJoules.

In some embodiments, for the predetermined pattern described with reference to FIG. 5B, an average laser power has a value between 100 milliWatts and 5000 milliWatts. In some embodiments, an average laser power has a value of 1000 MilliWatts.

In some embodiments, for the predetermined pattern described with reference to FIG. 5B, an average number of laser shots delivered on the patient's iris lies between 100,000 to 20 million. In some embodiments, an average number of laser shots delivered on the patient's iris is between 500,000 to 2 million.

Additional examples of laser parameters and operating conditions and ranges are as described below:

Number of laser-machined posterior features 50-300, (e.g., in some embodiments, a number of laser-machined posterior features is 100);

Size of posterior iris laser-machined individual feature 50-200 micrometers diameter features (e.g., 100 micrometers in diameter);

Depth of iris tissue treated: 50-200 micrometer deep features (e.g., 100 micrometer deep features);

Fraction of iris area treated: 1-20%;

Clinical laser exposure time: 30-120 seconds (e.g., 60 seconds);

Focusing condition (e.g., spot size) 0.3-0.6 NA (e.g., 0.4-0.5 NA); and/or

Separation of consecutive laser shots in scanning pattern: 1-10 micrometer, preferably 3-6 micrometer.

Figure 6A:
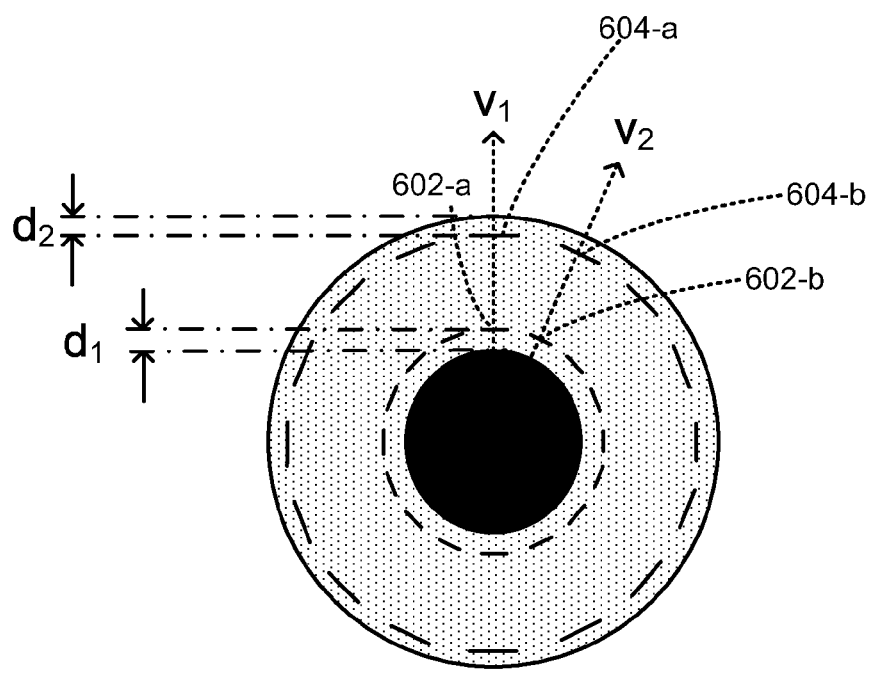
FIG. 6A-6B illustrate substantially circumferential predetermined patterns (e.g., in dual concentric arrangements) of positions for delivering the laser light beam on one or more of the iris tissues of a patient's eye, in accordance with some embodiments of the present disclosure.
Figure 6B:
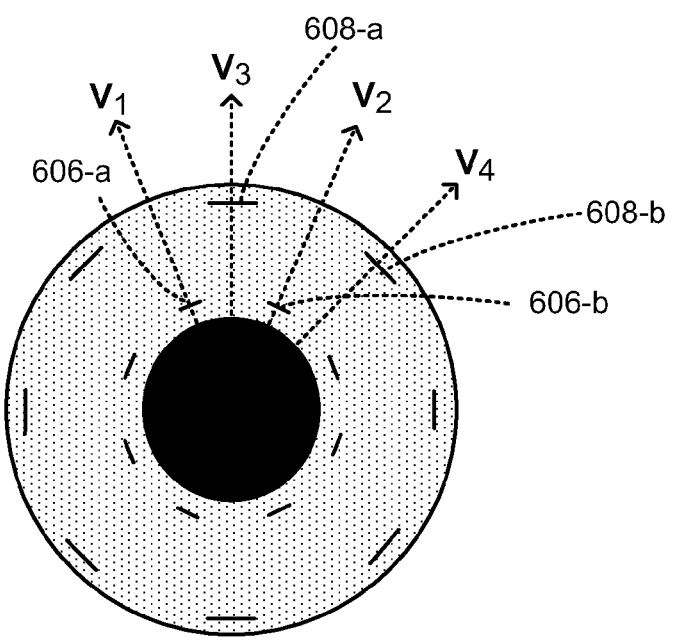

FIGS. 6A-6B illustrate substantially circumferential predetermined patterns (e.g., in dual concentric arrangements) of positions for delivering the laser light beam on one or more of the iris tissues of a patient's eye, in accordance with some embodiments of the present disclosure.

In some embodiments, the predetermined pattern is a substantially circumferential pattern. The plurality of positions comprises a (i) first set of M positions (e.g., positions 602-a, 602-b and the like where M=16, as shown in FIG. 6A; positions 606-a, 606-b and the like where M=8, as shown in FIG. 6B) and (ii) a second set of P positions (e.g., positions 604-a, 604-b and the like where P=16, as shown in FIG. 6A; positions 608-a, 608-b and the like where P=8, as shown in FIG. 6B).

Each position of the first set of M positions occurs at a first predetermined distance (e.g., distance $d_1$ as shown in FIG. 6A) along the radius of the iris measured from the inner circumference of the iris and the first set of M positions forms a first portion of the substantially circumferential pattern which is substantially concentric with and proximal to the inner circumference of the iris (e.g., proximal to the iris limbus; external and adjacent to the sphincter muscle, for example targeting the iris stromal tissue and/or the iris dilator muscles, as explained with reference to FIG. 2B).

Each position of the second set of P positions occurs at a second predetermined distance (e.g., distance $d_2$ as shown in FIG. 6A) along the radius of the iris measured from the outer circumference of the iris and the first set of P positions forming a second portion of the substantially circumferential pattern which is substantially concentric with and proximal to the outer circumference of the iris (e.g., proximal to the iris root, as explained with reference to FIG. 2B). In some embodiments, each position of the plurality of positions corresponds to a treatment zone (e.g., a cut) on the patient's iris using the laser light beam.

In some embodiments, the first predetermined distance has a value between 0.75 millimeters and 1.5 millimeters, the second predetermined distance has a value between 0 and 1.5 millimeters, and M and P are positive integers of values between 4 and 20.

FIG. 6A illustrates a substantially circumferential predetermined pattern of positions (e.g., in a dual concentric arrangement, with the positions placed in both concentric arrangements along the same radial vectors) for delivering the laser light beam on one or more of the iris tissues of a patient's eye, in accordance with some embodiments of the present disclosure.

In some embodiments, the first set of M positions includes (i) a first position (e.g., position 602-a, FIG. 6A) with a center located along a first radial vector (vector $v_1$, FIG. 6A) measured from the center of the pupil toward the outer circumference of the iris and (ii) a second position (e.g., position 602-b, FIG. 6A), adjacent to the first position among the first set of M positions, located along a second radial vector (vector $v_2$, FIG. 6A) measured from the center of the pupil toward the outer circumference of the iris. The second set of P positions includes a third position (e.g., position 604-a, FIG. 6A) along the first radial vector (vector $v_1$, FIG. 6A) and a fourth position (e.g., position 604-b, FIG. 6A) adjacent to the third position along the second radial vector (vector $v_2$, FIG. 6A).

FIG. 6B illustrates a substantially circumferential predetermined pattern of positions (e.g., in a dual concentric arrangement, with the positions placed in the two concentric arrangements along interleaved radial vectors) for delivering the laser light beam on one or more of the iris tissues of a patient's eye, in accordance with some embodiments of the present disclosure.

In some embodiments, the first set of M positions includes (i) a first position (e.g., position 606-a, FIG. 6B) with a center located along a first radial vector (vector $v_1$, FIG. 6B) measured from the center of the pupil toward the outer circumference of the iris and (ii) a second position (e.g., position 606-b, FIG. 6B), adjacent to the first position among the first set of M positions, located along a second radial vector (vector $v_2$, FIG. 6B) measured from the center of the pupil toward the outer circumference of the iris. The second set of P positions includes (i) a third position (e.g., position 608-a, FIG. 6B) along a third radial vector (vector $v_3$, FIG. 6B) and (ii) a fourth position (e.g., position 608-b, FIG. 6B) adjacent to the third position along the fourth radial vector (vector $v_4$, FIG. 6B). The third radial vector is located between the first radial vector and the second radial vector (e.g., $v_3$ is located between $v_1$ and $v_2$, FIG. 6B); and the second radial vector is located between the third radial vector and the fourth radial vector (e.g., $v_2$ is located between $v_3$ and $v_4$, FIG. 6B).

Figure 7:
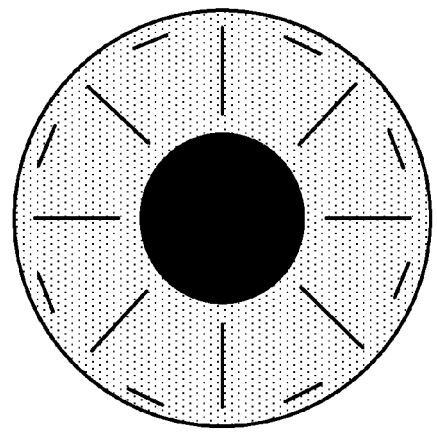
FIG. 7 illustrates a combination of substantially radial and substantially circumferential patterns of positions for delivering the laser light beam on one or more of the iris tissues of a patient's eye, in accordance with some embodiments of the present disclosure.

FIG. 7 illustrates a combination of substantially radial (e.g., as explained with reference to FIGS. 4A-4B) and substantially circumferential patterns (e.g., as explained with reference to FIGS. 5A-5B) of positions for delivering the laser light beam on one or more of the iris tissues of a patient's eye, in accordance with some embodiments of the present disclosure.

Figure 8:
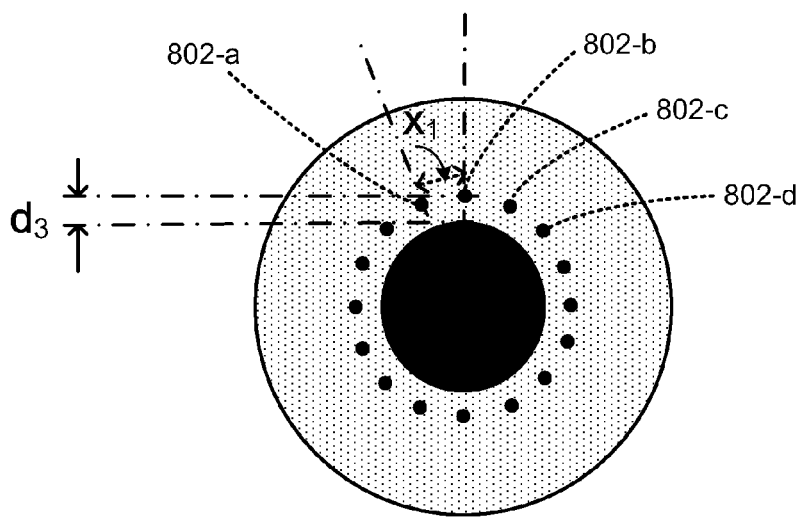
FIG. 8 illustrates a substantially circular predetermined spot pattern of positions for delivering the laser light beam on one or more of the iris tissues of a patient's eye, in accordance with some embodiments of the present disclosure.

FIG. 8 illustrates a substantially circular predetermined spot pattern of positions for delivering the laser light beam on one or more of the iris tissues of a patient's eye, in accordance with some embodiments of the present disclosure.

In some embodiments, the predetermined pattern is a substantially circular spot pattern. The plurality of positions comprises N positions (e.g., positions 802-1, 802-b, 502-c, and the like where N=16 as shown in FIG. 8), each of the N positions occurring at a third predetermined distance (e.g., distance $d_3$ as shown in FIG. 8) along a radius of the iris measured from the inner circumference of the iris. The N positions together form the substantially circular spot pattern which is substantially concentric with and proximal to the inner circumference of the iris (e.g., proximal to the iris limbus; external and adjacent to the sphincter muscle, for example targeting the iris stromal tissue and/or the iris dilator muscles, as explained with reference to FIG. 2B). The N positions include a first spot position (e.g., position 802-a, FIG. 8) and a second spot position (e.g., position 802-b, FIG. 8) adjacent to the first spot position, wherein a center of the first spot position is separated from a center of the second spot position by a predetermined separation (e.g., separation $x_1$ as shown in FIG. 8) along the circumferential pattern. In some embodiments, each position of the plurality of positions corresponds to a treatment zone (e.g., a cut) on the patient's iris using the laser light beam.

In some embodiments, the third predetermined distance has a value between 0.75 millimeters and 1.5 millimeters, the predetermined separation has a value between 0 micrometers and 300 micrometers, an average diameter of the first spot position has a value between 10 micrometers to 300 micrometers, and N is a positive integer of value between 4 and 20. In some embodiments, the laser light beam is focused on the plurality of positions, thereby cousin contraction of collagen in stroma and weakening of dilator muscle on the posterior iris.

In some embodiments, for the predetermined pattern described with reference to FIG. 8, a wavelength of the laser light beam has a value between 532 nanometers and 1100 nanometers. In some embodiments, a wavelength of the laser light beam has a value between 900 nanometers and 1064 nanometers.

In some embodiments, for the predetermined pattern described with reference to FIG. 8, the laser light source is a pulse laser and an average duration of laser pulses has a value between 10 milliseconds and 100 milliseconds. In some embodiments, an average duration of laser pulses has a value between 40 milliseconds and 60 milliseconds.

In some embodiments, for the predetermined pattern described with reference to FIG. 8, the laser light source is a pulse laser and an average repetition rate (e.g., frequency of repetition or pulsing) of laser pulses has a value between 2 Hertz and 40 Hertz. In some embodiments, an average repetition rate (e.g., frequency of repetition or pulsing) of laser pulses has a value between 5 Hertz and 15 Hertz.

In some embodiments, for the predetermined pattern described with reference to FIG. 8, the laser light source is a pulse laser and a laser peak power has a value between 0.5 Watt and 6 Watts. In some embodiments, the laser peak power has value of between 4 Watts and 6 Watts.

In some embodiments, for the predetermined pattern described with reference to FIG. 8, the laser light source is a pulse laser and an average laser pulse energy has a value between 5 milliJoules and 250 milliJoules. In some embodiments, an average laser pulse energy has a value between 80 milliJoules and 120 milliJoules.

In some embodiments, for the predetermined pattern described with reference to FIG. 8, an average laser power has a value between 0.2 Watt and 1 Watt. In some embodiments, an average laser power has a value between 0.4 Watt to 0.6 Watt.

In some embodiments, for the predetermined pattern described with reference to FIG. 8, an average number of laser shots delivered on the patient's iris lies between 100 and 1000. In some embodiments, an average number of laser shots delivered on the patient's iris is between 200 and 300.

Figure 9:
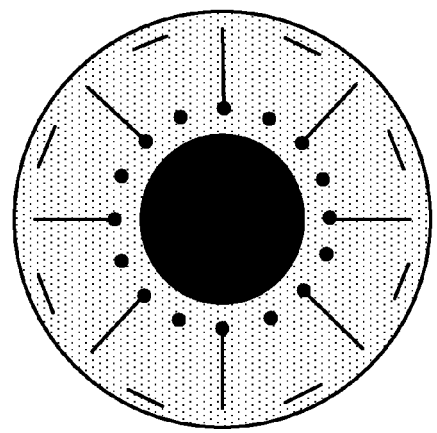
FIG. 9 illustrates a combination of substantially radial, substantially circumferential, and substantially circular spot patterns of positions for delivering the laser light beam on one or more of the iris tissues of a patient's eye, in accordance with some embodiments of the present disclosure.

Additional examples of laser parameters and operating conditions and ranges are as described below:
  Fraction of Iris to be treated: 1%-20% (e.g., 5-10%);
  Total Clinical treatment time: 15-120 seconds (e.g., 40-60 seconds);

Target Increase in Tissue Temperature: 10-60 degrees Celsius (e.g., target increase 35-45 degrees Celsius); and/or Spot Size of Treatment Zone: 40-350 micrometers (e.g., 150-260 micrometers);

FIG. 9 illustrates a combination of substantially radial (e.g., as explained with reference to FIGS. 4A-4B), substantially circumferential (e.g., as explained with reference to FIGS. 5A-5B), and substantially circular spot patterns (e.g., as explained with reference to FIG. 8) of positions for delivering the laser light beam on one or more of the iris tissues of a patient's eye, in accordance with some embodiments of the present disclosure.

Figure 10:
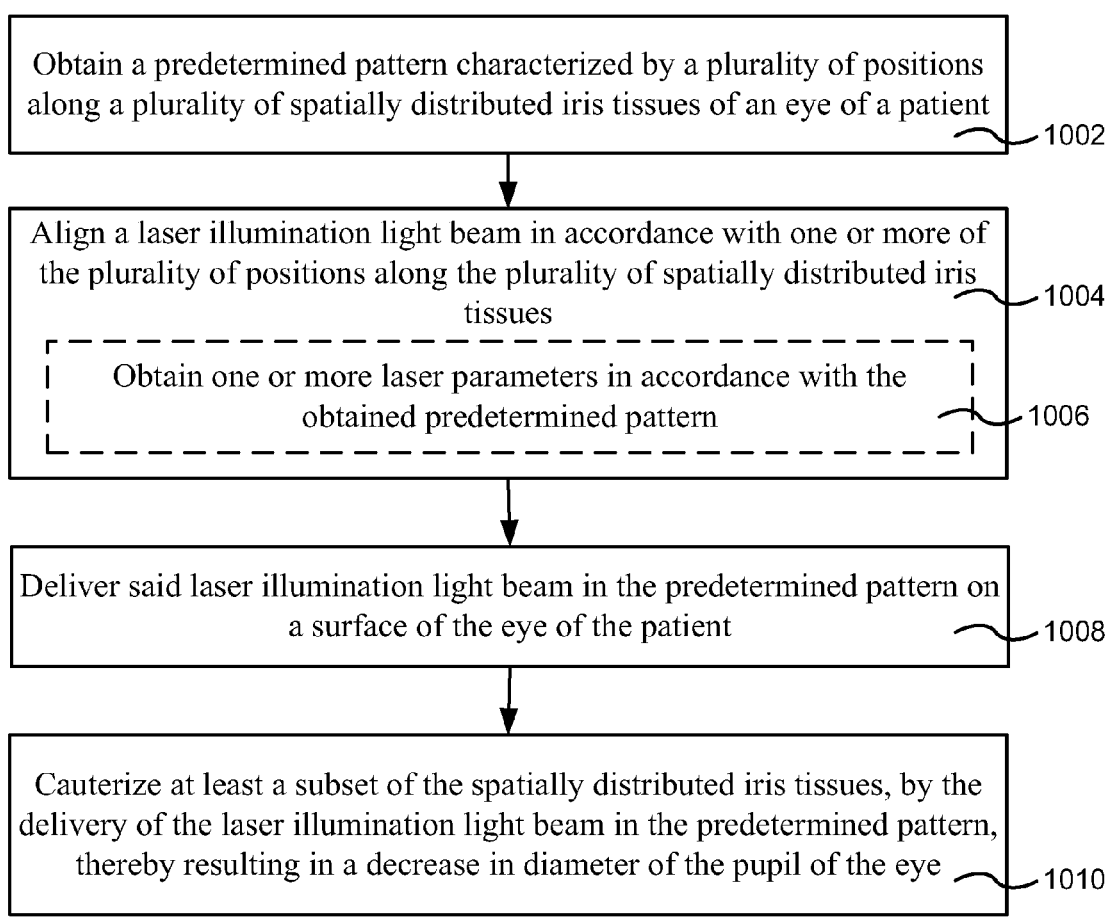
FIG. 10 is a flowchart illustrating a method for improving vision performed at an ophthalmic laser system, in accordance with some embodiments of the present disclosure.

FIG. 10 is a flowchart representing a method 1000 for improving vision performed at an ophthalmological laser system, according to certain embodiments of the invention. Method 1000 may be governed by instructions that are stored in a computer readable storage medium and that are executed by one or more processors of one or more servers. Each of the operations shown in FIG. 10 may correspond to instructions stored in a computer memory or computer readable storage medium. The computer readable storage medium may include a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors.

The ophthalmic laser system 100 obtains (e.g., retrieves and/or generates) (1002) a predetermined pattern characterized by a plurality of positions along a plurality of spatially distributed iris tissues of an eye of a patient. For example the ophthalmic laser system obtains a substantially radial pattern as described with reference to FIGS. 4A-4B, a substantially circumferential pattern as described with reference to FIGS. 5A-5B and 6A-6B, a combination of substantially radial and substantially circumferential patterns as described with reference to FIG. 7, a substantially circular spot pattern as described with reference to FIG. 8, a combination of substantially radial, substantially circumferential, or substantially circular spot patterns as described with reference to FIG. 9. The predetermined patterns are characterized by a corresponding plurality of positions (e.g., as described with reference to FIGS. 4A-4B, 5A-5B, 6A-6B, and 7-9) along a plurality of spatially distributed iris tissues (e.g., the iris limbus tissue, the iris stromal tissue, and/or the iris dilator muscle tissue; as described with reference to FIG. 2B).

Ophthalmic laser system 100 aligns (1004) a laser illumination light beam in accordance with one or more of the plurality of positions along a plurality of spatially distributed iris tissues. In some embodiments, ophthalmic laser system 100 obtains (1006) one or more laser parameters (e.g., wavelength of laser light, average duration of laser pulses, average pulse repetition rate of laser pulses, time of treatment or delivery of laser pulses, and the like; as explained with reference to FIG. 1, FIGS. 5A-5B, and FIG. 8) in accordance with the obtained predetermined pattern. In other words, in some embodiments, one or more of the laser parameters are selected in accordance with the predetermined pattern; different sets of laser parameters are selected for different corresponding predetermined patterns. If a combination of predetermined patterns is used (e.g., a combination of substantially radial and substantially circumferential patterns as shown in FIG. 7; or a combination of radial, substantially circumferential, and substantially circular spot patterns as shown in FIG. 9), then a corresponding combination of laser parameters are used in accordance with the selected combination of predetermined patterns.

Ophthalmic laser system 100 delivers (1008) the laser illumination light beam in the predetermined pattern on a surface of the eye of the patient.

Ophthalmic laser system 100 cauterizes (1010) (e.g., heats to a predefined temperature and/or treats) at least a subset of the spatially distributed iris tissues, by the delivery of the laser illumination light beam in the predetermined pattern (e.g., causing the subset of iris tissues to heat, contract, be cut, or scarify), thereby resulting in a decrease in diameter of the pupil of the eye.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An ophthalmological laser system comprising:
a laser, the radiation of which is focusable as a laser illumination light beam, wherein the laser is a pulse laser and the laser illumination light beam comprises a sequence of light pulses of average time duration between 10 milliseconds and 100 milliseconds;
at least one processor;
memory;
at least one program stored in the memory and executable by the at least one processor, the at least one program comprising instructions to:
obtain a predetermined pattern characterized by a plurality of positions along an iris dilator muscle tissue of an eye of a patient;
align said laser illumination light beam in accordance with one or more of the plurality of positions along the iris dilator muscle tissue;
deliver said laser illumination light beam in the predetermined pattern on a surface of the eye of the patient to target the iris dilator muscle tissue; and
cauterize at least a subset of the iris dilator muscle tissue to weaken dilator muscle, by the delivery of the laser illumination light beam in the predetermined pattern, thereby resulting in a permanent decrease in diameter of the pupil of the eye.

2. The ophthalmological system of claim 1, wherein the laser is a pulse laser and the laser illumination light beam comprises a sequence of a plurality of light pulses with an average repetition rate between two consecutive light pulses of the plurality of light pulses between 0.5 Hertz and 100 kiloHertz.

3. The ophthalmological system of claim 1, wherein said laser illumination light beam comprises laser light of wavelength between 500 nanometers and 1700 nanometers.

4. The ophthalmological system of claim 1, wherein the obtained predetermined pattern further defines one or more laser parameters and wherein the instructions to deliver said laser illumination light deliver the laser illumination light in accordance with the one or more laser parameters.

5. The ophthalmological system of claim 1, wherein the predetermined pattern includes one or more of: a substantially radial pattern, a substantially circumferential pattern, a substantially circular spot pattern, or any combination thereof.

6. The ophthalmological system of claim 1, wherein:
the predetermined pattern is a substantially radial pattern;
the plurality of positions comprise N positions, each of the N positions oriented radially from the inner circumference of the iris proximal to the pupil to the outer circumference of the iris distal to the pupil; and
the N positions include a first position and a second position, the second position being adjacent to the first position and separated from the first position by a predefined angular separation.

7. The ophthalmological system of claim 6, wherein the predefined angular separation has a value between 10° and 50° and N is a positive integer of value between 4 and 36.

8. The ophthalmological system of claim 1, wherein:
the predetermined pattern is a substantially circumferential pattern;
the plurality of positions comprises N positions, each of the N positions occurring at a first predetermined distance along a radius of the iris measured from inner circumference of the iris;
the N positions together form the substantially circumferential pattern which is substantially concentric with and proximal to the inner circumference of the iris; and
the N positions include a first position and a second position adjacent to the first position, wherein a center of the first position is separated from a center of the second position by a predetermined separation along the circumferential pattern.

9. The ophthalmological system of claim 8, wherein the first predetermined distance has a value between 0.75 millimeters and 1.5 millimeters, the predetermined separation has a value between 50 micrometers and 300 micrometers, an average length of the first position has a value between 25 micrometers and 200 micrometers, and N is a positive integer of value between 4 and 20.

10. The ophthalmological system of claim 1, wherein:
the predetermined pattern is a substantially circumferential pattern;
the plurality of positions comprises N positions, each of the N positions occurring at a second predetermined distance along a radius of the iris measured from the outer circumference of the iris;
the N positions together form the substantially circumferential pattern which is substantially concentric with and proximal to the outer circumference of the iris; and
the N positions include a first position and a second position adjacent to the first position, wherein a center of the first position is separated from a center of the second position by a predetermined separation along the circumferential pattern.

11. The ophthalmological system of claim 10, wherein the second predetermined distance has a value between 0 and 1.5 millimeters, the predetermined separation has a value between 50 micrometers and 1 millimeter, an average length of the first position has a value between 25 micrometers and 500 micrometers, and N is a positive integer of value between 4 and 20.

12. The ophthalmological system of claim 1, wherein:
the predetermined pattern is a substantially circular spot pattern;
the plurality of positions comprises N positions, each of the N positions occurring at a predetermined distance along a radius of the iris measured from the inner circumference of the iris;
the N positions together form the substantially circular spot pattern which is substantially concentric with and proximal to the inner circumference of the iris; and
the N positions include a first spot position and a second spot position, the second spot position being adjacent to the first spot position, wherein a center of the first spot position is separated from a center of the second spot position by a predetermined separation along the substantially circular spot pattern.

13. The ophthalmological system of claim 12, wherein the predetermined distance has a value between 0.75 millimeters and 1.5 millimeters, the predetermined separation has a value less than 300 micrometers, an average radius of the first spot position has a value between 10 micrometers to 300 micrometers, and N is a positive integer of value between 4 and 20.

14. The ophthalmological system of claim 1, wherein:
the predetermined pattern is a substantially circumferential pattern; and
the plurality of positions comprises a (i) first set of M positions and (ii) a second set of P positions wherein:
each position of the first set of M positions occurs at a first predetermined distance along the radius of the iris measured from the inner circumference of the iris and the first set of M positions forms a first portion of the substantially circumferential pattern which is substantially concentric with and proximal to the inner circumference of the iris; and
each position of the second set of P positions occurs at a second predetermined distance along the radius of the iris measured from the outer circumference of the iris and the first set of P positions forms a second portion of the substantially circumferential pattern which is substantially concentric with and proximal to the outer circumference of the iris.

15. The ophthalmological system of claim 14, wherein:
the first set of M positions includes (i) a first position with a center located along a first radial vector measured from the center of the pupil toward the outer circumference of the iris and (ii) a second position, adjacent to the first position among the first set of M positions, located along a second radial vector measured from the center of the pupil toward the outer circumference of the iris; and
the second set of P positions includes a third position along the first radial vector and a fourth position adjacent to the third position along the second radial vector.

16. The ophthalmological system of claim 14, wherein:
the first set of M positions includes (i) a first position with a center located along a first radial vector measured from the center of the pupil toward the outer circumference of the iris and (ii) a second position, adjacent to the first position among the first set of M positions, located along a second radial vector measured from the center of the pupil toward the outer circumference of the iris;
the second set of P positions includes (i) a third position along a third radial vector and (ii) a fourth position adjacent to the third position along the fourth radial vector;
the third radial vector is located between the first radial vector and the second radial vector; and
the second radial vector is located between the third radial vector and the fourth radial vector.

17. The ophthalmological system of claim 14, wherein the first predetermined distance has a value between 0.75 millimeters and 1.5 millimeters, the second predetermined distance has a value between 0 and 1.5 millimeters, and M and P are positive integers of values between 4 and 20.

18. A non-transitory computer readable storage medium storing one or more programs configured for execution by a computer, the one or more programs comprising instructions to:
  obtain a predetermined pattern characterized by a plurality of positions along an iris dilator muscle tissue of an eye of a patient;
  align a laser illumination light beam in accordance with one or more of the plurality of positions along the iris dilator muscle tissue, wherein the laser illumination light beam comprises a sequence of light pulses of average time duration between 10 milliseconds and 100 milliseconds;
  deliver said laser illumination light beam in the predetermined pattern on a surface of the eye of the patient to target the iris dilator muscle tissue; and
  cauterize at least a subset of the iris dilator muscle tissue to weaken dilator muscle, by the delivery of the laser illumination light beam in the predetermined pattern, thereby resulting in a permanently decrease in diameter of the pupil of the eye.

19. A method of improving vision performed using an ophthalmological laser system, the method comprising:
  obtaining a predetermined pattern characterized by a plurality of positions along an iris dilator muscle tissue of an eye of a patient;
  aligning a laser illumination light beam in accordance with one or more of the plurality of positions along the iris dilator muscle tissue, wherein the laser illumination light beam comprises a sequence of light pulses of average time duration between 10 milliseconds and 100 milliseconds;
  delivering said laser illumination light beam in the predetermined pattern on a surface of the eye of the patient to target the iris dilator muscle tissue; and
  cauterizing at least a subset of the iris dilator muscle tissue to weaken dilator muscle, by the delivery of the laser illumination light beam in the predetermined pattern, thereby resulting in a permanent decrease in diameter of the pupil of the eye.

20. The ophthalmological system of claim 12, wherein the laser illumination light beam comprises laser light of wavelength between 532 nanometers and 1100 nanometers.

21. The ophthalmological system of claim 12, wherein the laser illumination light beam comprises laser light of wavelength between 900 nanometers and 1064 nanometers.

22. The ophthalmological system of claim 12, wherein the laser is a pulse laser and the laser illumination light beam comprises a laser peak power of between 0.5 Watt and 6 Watts.

23. The ophthalmological system of claim 12, wherein the average number of laser shots delivered on the iris of the patient is between 100 and 1000.

24. The ophthalmological system of claim 12, wherein the average number of laser shots delivered on the iris of the patient is between 200 and 300.

* * * * *